(12) United States Patent
Arramon et al.

(10) Patent No.: US 6,875,219 B2
(45) Date of Patent: Apr. 5, 2005

(54) BONE ACCESS SYSTEM

(76) Inventors: Yves P. Arramon, 207 Oakland Ave., Apt. #1, Capitola, CA (US) 95010; Scott H. McIntyre, 30 Cherry Crest La., San Jose, CA (US) 95136

(*) Notice: Subject to any disclaimer, the term of this patent is extended or adjusted under 35 U.S.C. 154(b) by 50 days.

(21) Appl. No.: 10/366,992

(22) Filed: Feb. 14, 2003

(65) Prior Publication Data

US 2004/0162559 A1 Aug. 19, 2004

(51) Int. Cl.⁷ ............................................. A61B 17/34
(52) U.S. Cl. ......................................... 606/92; 606/185
(58) Field of Search ...................... 604/164.01, 164.11, 604/164.13, 170.02, 264, 170.03, 158; 606/191, 185, 92, 190

(56) References Cited

U.S. PATENT DOCUMENTS

| | | | |
|---|---|---|---|
| 4,969,888 A | | 11/1990 | Scholten et al. |
| 5,108,404 A | | 4/1992 | Scholten et al. |
| 5,304,141 A | * | 4/1994 | Johnson et al. ............. 604/158 |
| 5,830,188 A | * | 11/1998 | Abouleish .................... 604/158 |
| 6,019,776 A | | 2/2000 | Preissman et al. |
| 6,033,411 A | | 3/2000 | Preissman |
| 6,248,110 B1 | | 6/2001 | Reiley et al. |
| 6,280,458 B1 | | 8/2001 | Boche et al. |
| 6,425,887 B1 | | 7/2002 | McGuckin et al. |
| 6,595,958 B1 | * | 7/2003 | Mickley ................ 604/164.01 |

OTHER PUBLICATIONS

Cybulski, George R. "Methods of Surgical Stabilization for Metastatic Disease of the Spine" Neurosurgery 1989; 25:240–252.

Deramond et al. "Percutaneous Vertebroplasty with Methyl–Methacrylate; Technique Method Results [abstract]," Radiology 1990; 117 (Suppl.): 352.

Harrington, Kevin D. "Anterior Decompression and Stabilization of the Spine as a Treatment for Vertebral Collapse and Spinal Cord Compression form Metastatic Malignancy" Clinical Orthopaedics and Related Research 1988; 233:177–197.

Sundaresan, et al. "Treatment of Neoplastic Epidural Cord Compression By Vertebral Body Resection and Stabilization." J Neurosurg 1985; 63:676–684.

* cited by examiner

Primary Examiner—David O. Reip
Assistant Examiner—D. Jacob Davis
(74) Attorney, Agent, or Firm—John T. Raffle; Richard R. Batt

(57) ABSTRACT

Instruments and methodology for nonlinear access to bone tissue sites are described. Embodiments disclosed include a conduit for delivering material or a medical device to a site and a core member that is able to steer the conduit and allow the combination to be advanced thorough cancellous bone. A cannula and stylet may be provided to first advance through hard bone. The core member includes a curved tip that may be straightened by the cannula or an actuator sheath to vary sweep of the curve. An obturator may be included in the system. This instrument may include a flexible portion as well. Each of the obturator and conduit may be provided with any of a variety of active tips. The systems may be used to perform hard tissue site implantation, for example, in connection with a high pressure injection system.

17 Claims, 9 Drawing Sheets

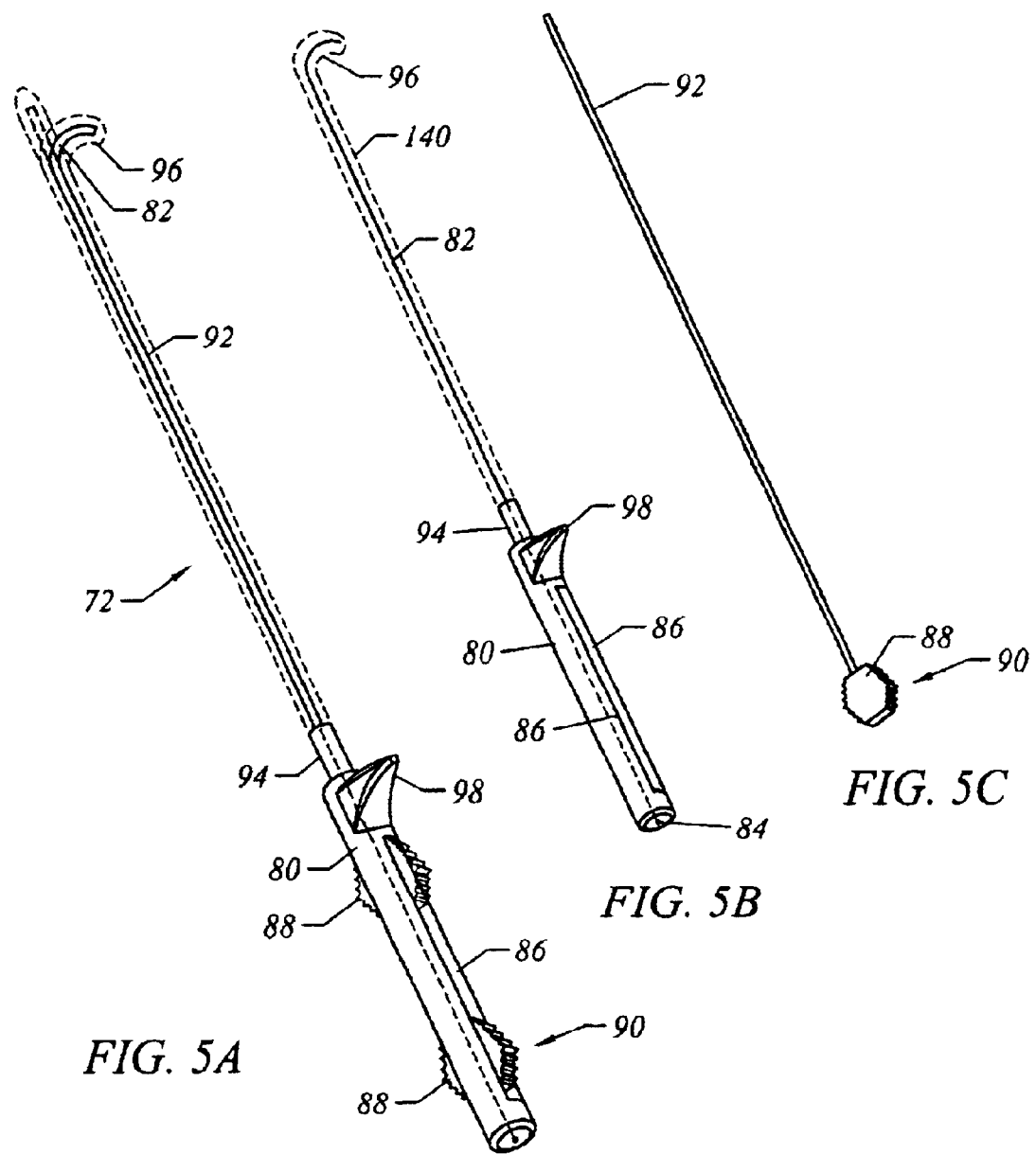

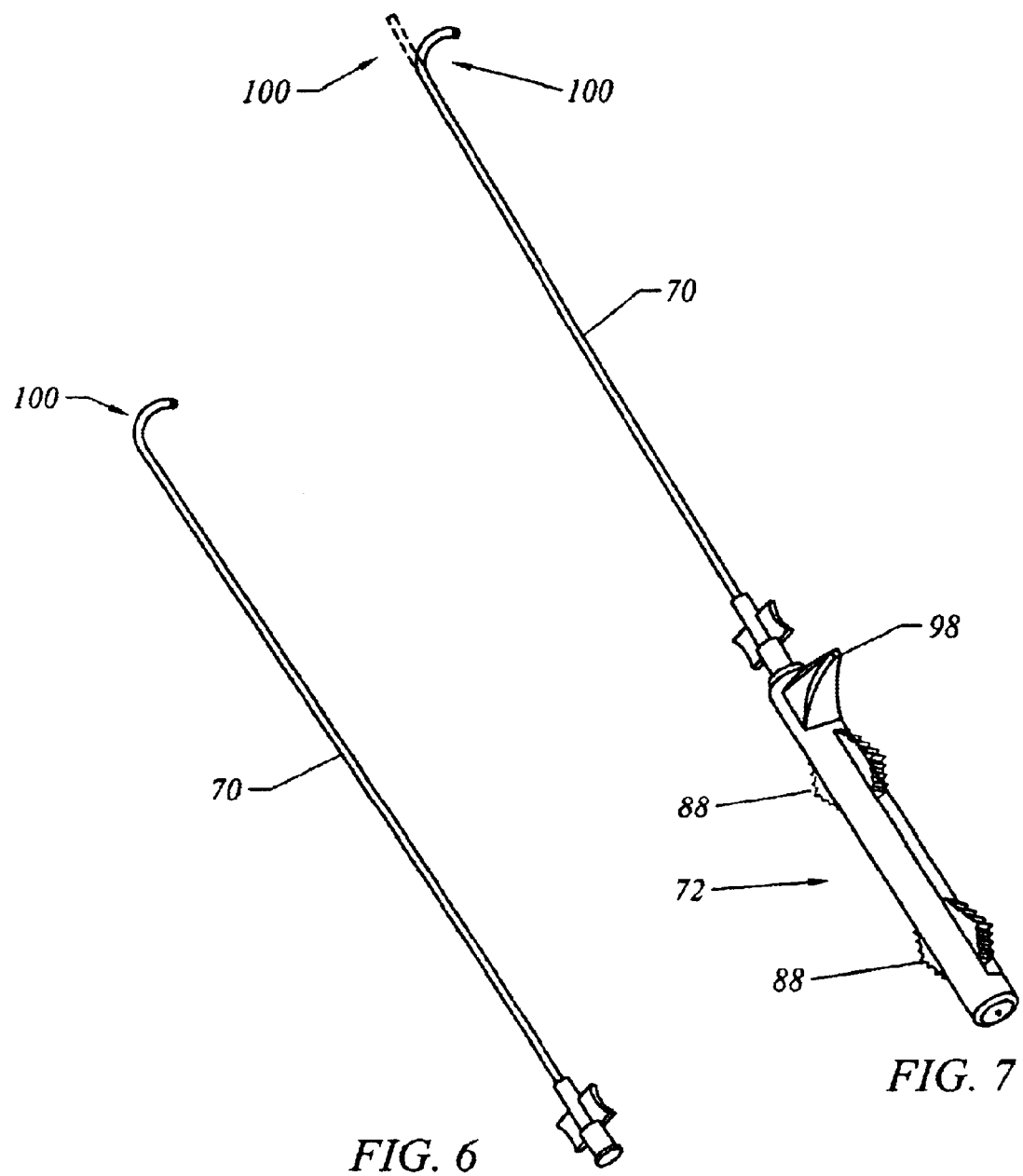

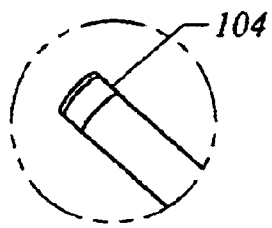
FIG. 9A
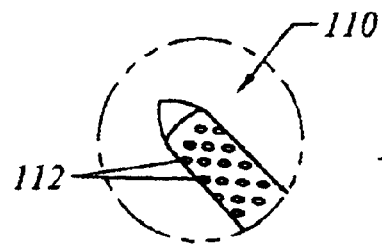
FIG. 9C
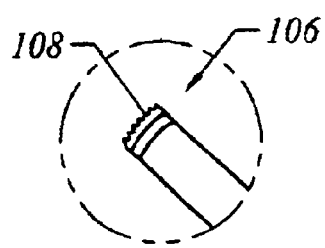
FIG. 9B
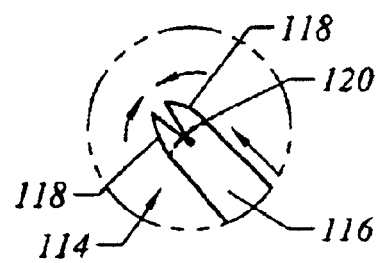
FIG. 9D
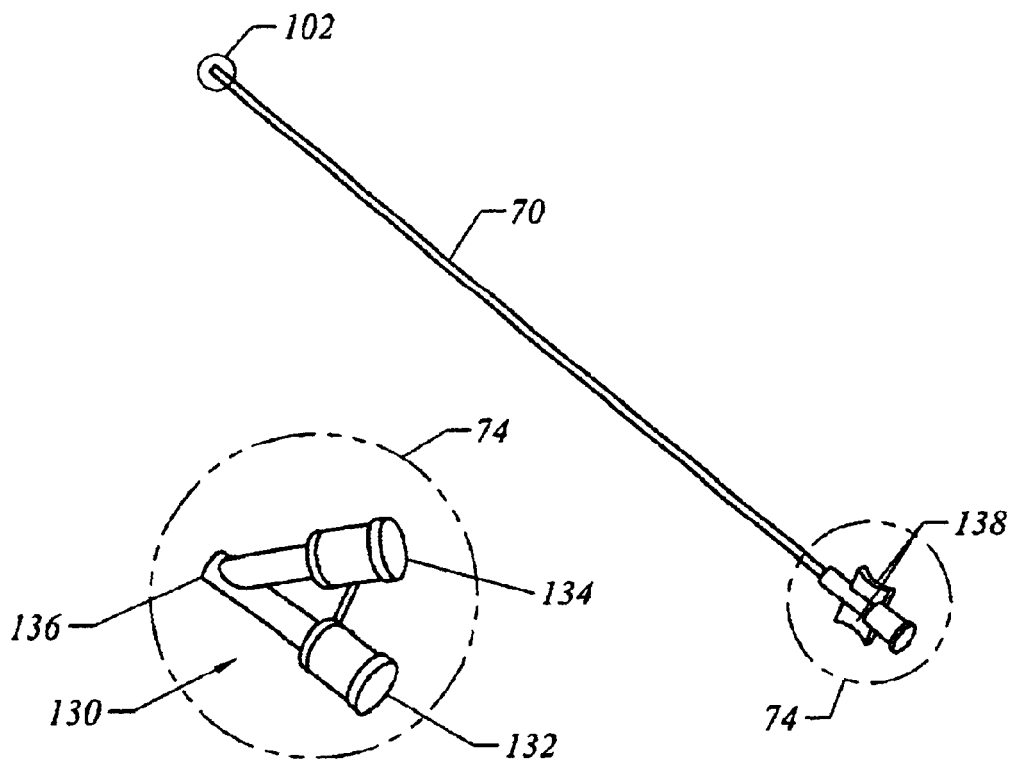
FIG. 8
FIG. 10

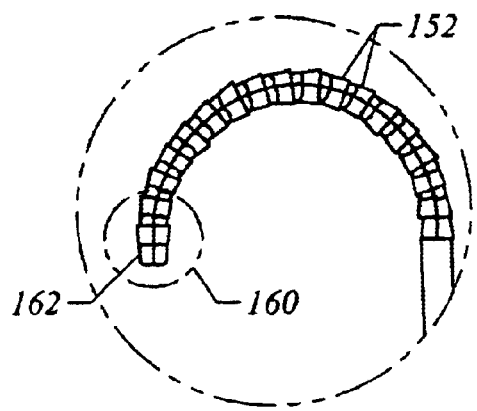
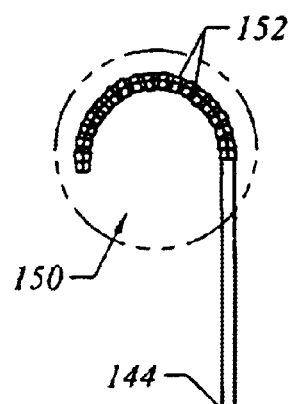
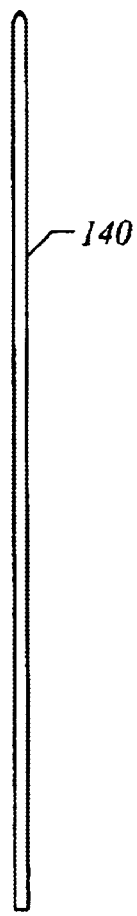
FIG. 13
FIG. 11
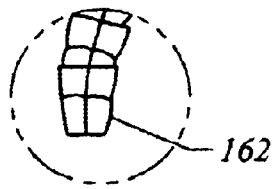
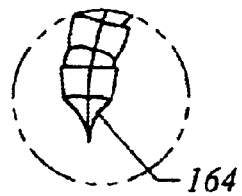
FIG. 14A  FIG. 14B
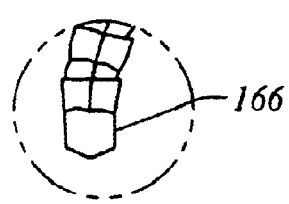
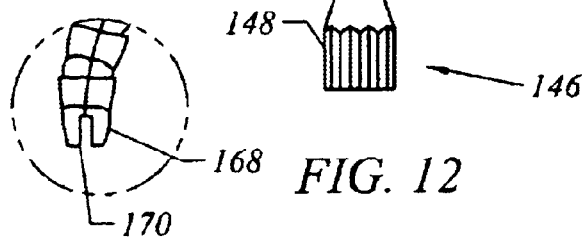
FIG. 14C  FIG. 14D  FIG. 12

BONE ACCESS SYSTEM

FIELD OF THE INVENTION

This invention relates to apparatus for accessing bone for conveying fluids, solids or medical devices thereto. More particularly, it involves a system for access to bone or other hard tissue, where the system has a manipulable or steerable end to reach radially disposed sites.

BRIEF DESCRIPTION OF THE DRAWINGS

FIGS. 2–16B diagrammatically illustrate aspects of the present invention. Variation of the invention from that shown in the figures is contemplated.

FIG. 1 is a plan view of various bone access tools sold by Cook Medical, Inc.

FIG. 2 is a perspective view of a high pressure injection system that may be used in connection with the present invention.

FIGS. 4A–4C" are perspective views in which FIGS. 4A and 4B show access and implant material delivery in a vertebral body site, respectively; FIGS. 4C–4C" depict varying access approaches in a long-bone application.

FIGS. 5A–5C are perspective views of manipulator components.

FIG. 6 is a perspective view of a catheter/conduit with a curved end.

FIG. 7 is a perspective view of a manipulator-conduit combination.

FIG. 8 is a perspective view of a straight catheter/conduit.

FIGS. 9A–9D are perspective views of various tips for a conduit.

FIG. 10 is a perspective view of an alternate introduction section from that shown in FIG. 8 for the conduit pictured.

FIG. 11 is a perspective view of an obturator usable in the present invention.

FIG. 12 is a perspective view of an alternate obturator with a flexible distal end; FIG. 13 is a close-up of the obturator distal end shown in FIG. 12.

FIGS. 14A–14D are perspective views of active tips for an obturator.

BACKGROUND OF THE INVENTION

The mineralized tissue of the bones of the human skeletal system are generally categorized into two morphological groups: "cortical" bone and "cancellous" bone. The outer walls of all bones are composed of cortical or "compact" bone. This tissue is characterized by a dense structure with only microscopic porosity. Cancellous or "trabecular" bone is found in the interior of bones. This tissue is composed of a lattice of interconnected slender rods and plates called "trabeculae."

Injectable Polymethylmethacrylate (PMMA), set within the trabeculae, has been used for supplementing cancellous bone, especially for anterior and posterior stabilization of the spine in metastatic disease. See Sundaresan, et al., "Treatment of neoplastic epidural cord compression by vertebral body resection and stabilization," J Neurosurg 1985;63:676–684; Harrington, "Anterior decompression and stabilization of the spine as a treatment for vertebral collapse and spinal cord compression from metastatic malignancy." Clinical Orthodpaedics and Related Research 1988;233:177–197; and Cybulski, "Methods of surgical stabilization for metastatic disease of the spine." Neurosurgery 1989;25:240–252. Deramond et al., "Percutaneous vertebroplasty with methyl-methacrylate: technique, method, results [abstract]," Radiology 1990; 117 (suppl): 352, among others, have described the percutaneous injection of PMMA into vertebral compression fractures by the transpedicular or paravertebral approach under CT and/or fluoroscopic guidance.

Percutaneous vertebroplasty is desirable from the standpoint that it is minimally invasive as compared to the alternative of surgically exposing a hard tissue site to be supplemented with PMMA or other filler. Several procedures are known for accessing a desired site in the cancellous bone of a vertebral body (or for that matter other cancellous bone) to deliver hard tissue implant material to stabilize—or build up—a site once expanded as taught by U.S. Pat. Nos. 6,280,456; 6,248,110; 5,108,404 and 4,969,888.

To gain access to a hard tissue implantation site, as described in U.S. Pat. No. 6,019,776 and 6,033,411, a straight needle or cannula in combination with a stylet may be employed. Once access is achieved and the stylet is removed from the cannula, hard tissue implant material is delivered through the same.

Figure 1:
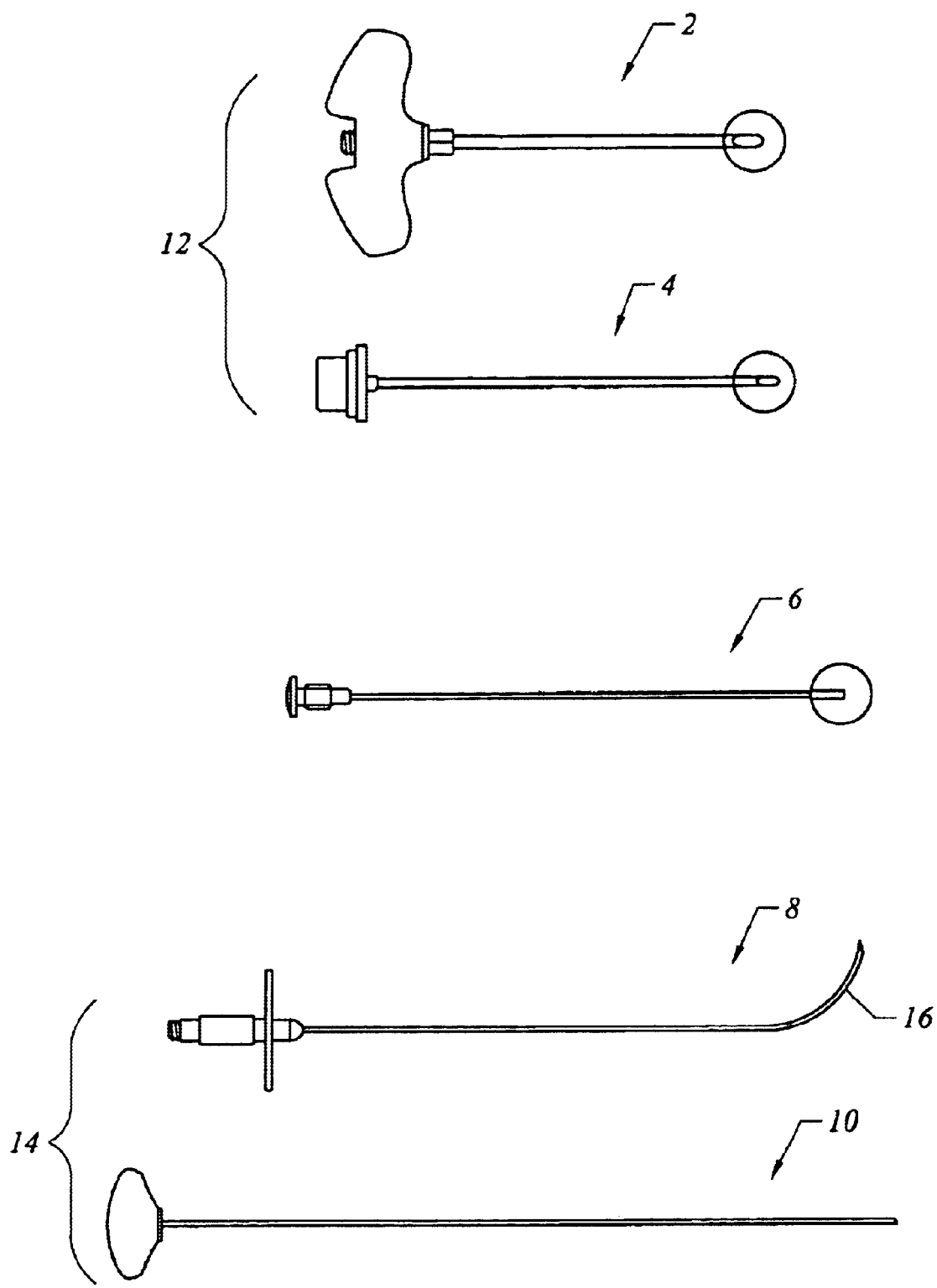
FIG. 1 represents information known in the art and is referenced in the Background of the Invention.

Another approach for biopsy sampling or material infusion is employed with a product sold by Cook Medical, Inc. The approach involves the use of a straight cannula/stylet combination for gaining access to the cancellous bone and a curved Nitinol (NiTi) needle for accessing a site that is radially oriented from the end of the cannula. The full set of instruments sold by Cook under the OSTEO-RX™ produce line is shown in FIG. 1. It includes straight cannula 2, a stylet 4 and obturator 6 for receipt in the cannula—each made of stainless steel. It further includes a curved Nitinol needle 8 and a flexible stylet 10 for receipt in the curved needle. The cannula/introducer needle 2 is a 10-gage member, 10 cm in length; the curved needle is a 13-gage member, 19 cm in length.

In use, cancellous bone tissue is accessed by traversing compact bone tissue with the stylet/cannula combination 12, each having a beveled end as highlighted in the magnified end images. Once a desired depth within the bone is reached, the stylet is withdrawn. The obturator 6 may be placed in cannula 2 in order to close-off the cavity temporarily or clear out tissue invading its space upon withdrawal of stylet 4. At this point, curved needle 8 is introduced into cannula 2.

Made of superelastic material, the needle straightens as the walls of the cannula apply force against it. Whether stylet 10 is inserted before or after loading the cannula with the curved (now straightened) needle 8, the combination is advanced in cannula 2 so that the distal end of the stylet, needle combination 14 bores through cancellous bone tissue a the desired delivery site. At this point, stylet 10 is removed to allow infusion of implant material under pressure to the site. Alternately, stylet 10 is only partially withdrawn and needle 8 advanced further to take a biopsy sample.

Whatever the intent of the procedure, needle 8 is then withdrawn at least into the body of the cannula so the straight cannula section may then be removed from the patient's body. For certain reasons, it may be desirable to remove the needle from the cannula altogether, e.g. for later infusion of material through the canula when the needle is used for acquiring a biopsy sample. In either case, no conduit is left behind to allow infusion of an implant material specifically at the end of the curved needle's tract.

Especially when withdrawing the curved needle from the cannula (but also in loading it into the cannula), the system presents high risk to users. It has been observed that the stiffness of curved needle 8 and amount of energy it stores upon straightening mandates extreme caution in handling, lest injury result from its curved end 16 returning to its unconstrained, curved shape—impaling the user. In addition to the user safety issues the device presents, the difficulty presented in straightening needle 8 within cannula 4 produces significant frictional forces between the members resulting in less than optimal actuation and control of the system. Furthermore, the insertion or removal (at least partial removal) activity of the curved needle into and out of the cannula occurs when cannula 2 is set within a patient's body makes any such manipulation more difficult.

Except for the present invention, no known solution has been developed that provides functionality like the above-referenced system, but without the noted problems with safety and ease use. As such, the present invention is particularly suited to meet the needs of bone access at sites that are radially located from an access path through harder bone tissue. It does so through operation principles which differ from those of the Cook system. Accordingly, a conduit and core member used in the present invention each differ in their unstressed shape and material properties as compared to those in the other system.

SUMMARY OF THE INVENTION

The present invention is a bone access system offering radial access to sites with reduced user risk and ease of use. The inventive system employs a flexible (semi-rigid) conduit that is formed into a curved shape by a curved core wire once the end of each item is advanced beyond the end of a cannula which restrains the core member (via the intermediately-located conduit). The core wire has a relatively low stiffness so it is easily set within the cannula (either together with the conduit or after the conduit has been placed therein). Various types of material may be employed for the curved core wire or guide wire including titanium, nickel-titanium, steel alloys or plastic/composite members.

In any case, the core member can be engineered to have a stiffness much lower than the curved needle in the above-reference Cook device since it need not be a large tubular member capable of delivering material therethrough. In the present invention, that task is left to the flexible conduit that is directed by the core member.

Additionally, the present invention is suited for use with an actuation sheath between the core member and conduit that is capable of independently straightening the preformed section of the wire. This allows for articulation of the curve independent of its relation to the end of the cannula. Yet another aspect of the invention provides an active tip (e.g., a drill bit or chisel) at the end of the core member. Such an active tip may be actuated by twisting, oscillating or other motion relative to the conduit to assist in advancing the co-axial conduit through bony matter. Still further, the invention may employ a serrated conduit end, possibly provided by a metal crown to assist in obtaining a bone biopsy sample.

A cannula (usually with a stylet) is used to provide a desired straight-line access path through hard bone. Then, the conduit and core wire of the present invention are advanced together to traverse cancellous bone to reach a desired site positioned radially from the end of the cannula. Upon removal of the core member, flowable material, a medical device, etc., may be introduced through the conduit. Alternately, a biopsy sample may be obtained once the core member is retracted.

Whatever the case, the present invention includes systems comprising any of the features described herein. Methodology described in association with the devices disclosed also forms part of the invention. Such methodology may include that associated with completing a vertebroplasty procedure and use of such auxiliary equipment as described below or otherwise available. The invention may be used in other methods as well. For instance, the invention further comprises such hardware and methodology as may be used in connection with that described which is incorporated by reference.

DETAILED DESCRIPTION OF THE INVENTION

Before the present invention is described in detail, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

Figure 2:
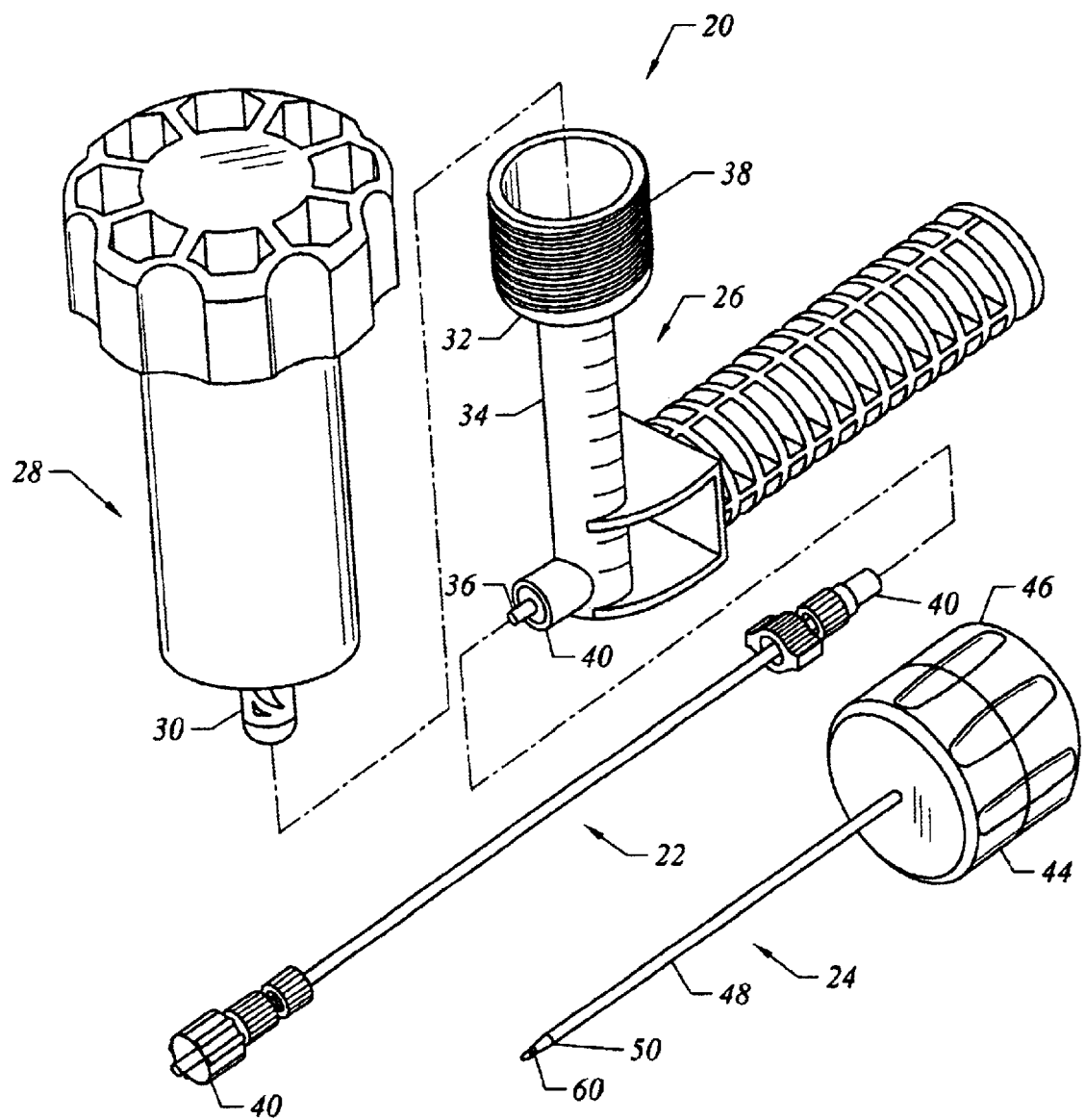

Turning now to FIG. 2, a system suitable for vertebroplasty or another hard tissue implantation procedure is shown. The system includes a high pressure applicator 20 comprising first and second columns, a conduit 22 for connection to the applicator and a cannula/stylet combination 24.

Applicator 20 comprises a first column 26 and a second column 28. A plunger head 30 is sized to freely pass into introduction section 32 (to avoid trapping air bubbles) and into a vessel section 34 where a frictional seal may be formed. The plunger is driven forward to extrude implant material provided within the vessel section out of nozzle 36. This may be accomplished via a threaded section 38 and a mating interface (not shown) within column 28 or otherwise. Further examples of acceptable pressure applicators for hard tissue implantation applications are provided in U.S. Pat. No. 6,383,190 which is incorporated herein by reference.

For use in vertebroplasty and other bone augmentation procedures, PMMA implant material may be preferred. Preferably, compositions as described in U.S. Pat. Nos. 6,232,615 and 6,309,420, each incorporated herein by reference, including contrast agent and particles to facilitate tracking the progress of injected material in-process are employed.

Figures 3A, 3B, 3C:
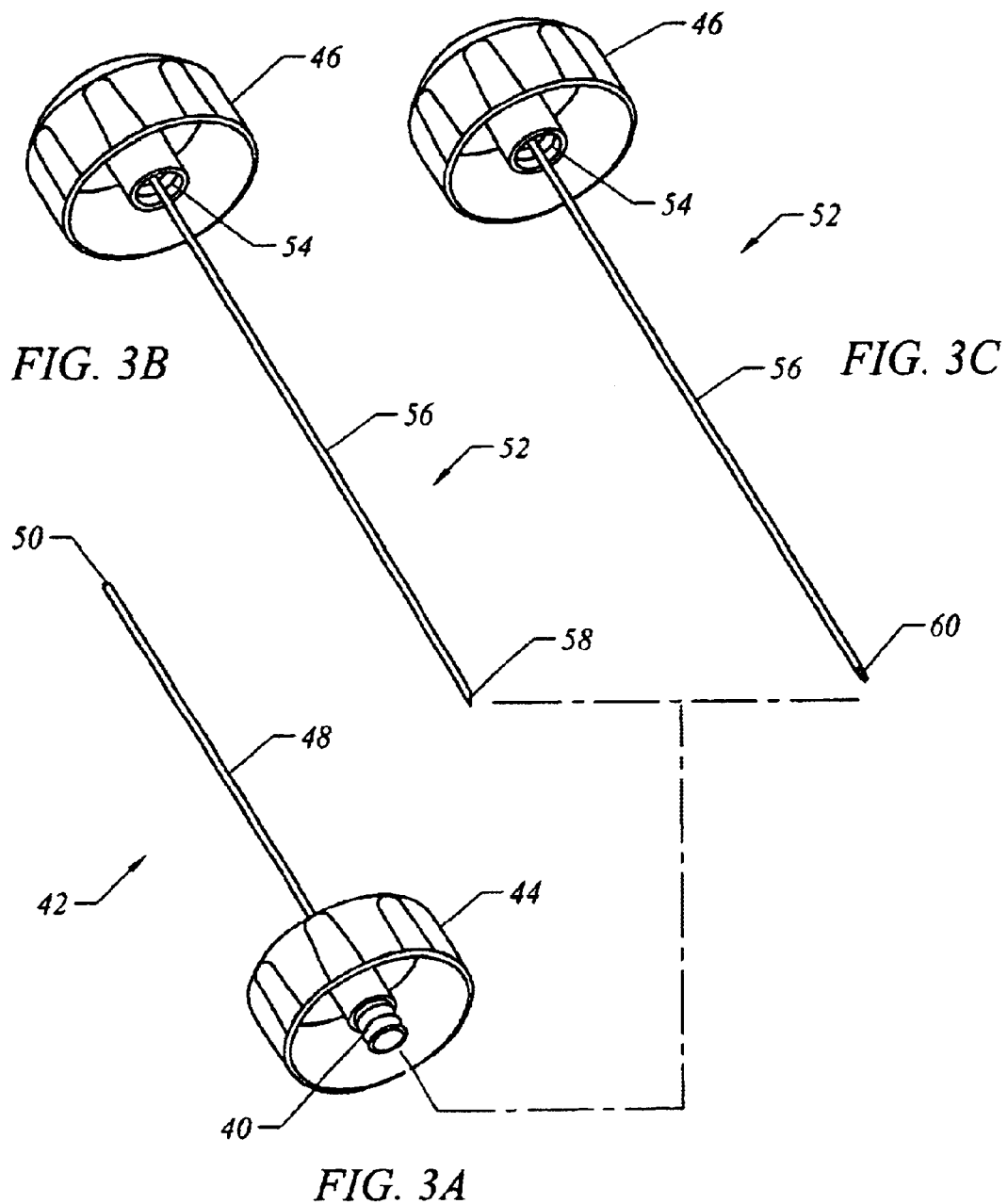
FIGS. 3A–3C are perspective views of a cannula and stylets that may be used with the high pressure injection system.

A non-compliant tube 22 is preferably provided for connection to the pressure application as shown (possibly via luer fittings 40) to allow remote delivery of implant material via a cannula 42 as shown in FIG. 3A. The cannula may be attached to the conduit using a complimentary luer fitting 40 or otherwise. Details regarding and advantages of utilizing a non-compliant delivery conduit are set forth in U.S. Pat. No. 6,348,055.

As provided in further detail in FIGS. 3A–3B, the cannula/stylet combination includes a cannula with handle portions 44 and a tubular body 48. The tubular portion includes a chamfered end 50. The stylet 52 shown in FIG. 3B also includes a handle portion 46 and includes threads 54 to interface with threads 40 on handle portion 44 of the cannula. A stylet shaft 56 that terminates in a single-beveled tip 58 is shown in FIG. 3B. The stylet 52 in FIG. 3C terminates in a threaded distal tip 60. Other suitable stylet configurations, such as sold by the assignee of the present invention and as described in U.S. Pat. No. 6,033,411 and U.S. patent application Ser. No. 09/409,948, filed Sep. 30, 1999, each entitled, "Precision Depth Guided Instruments For Use In Vertebroplasty," or U.S. patent application Ser. No. 09/876,387, entitled, "Cannula System of Hard Tissue Implant Delivery," filed Jun. 6, 2001, all of which are incorporated herein by reference, may be employed.

With such tools adapted for precutaneous bone access, a surgeon initially identifies a landmark with the aid of fluoroscopy of other imaging technique. Next, an injection is given to anesthetize the skin where insertion will occur. Local anesthesia will typically also be administered to the target site as well. After sufficient time has passed to effectively anesthetize the skin, an incision is made through the skin with a scalpel.

A combined stylet and cannula combination 24 is then inserted through the incision and advanced using a translation motion with no torquing, until the tip 60 of the stylet abuts the hard bone tissue to be traversed. Once contact has been made, the cannula tube is then grasped with a pair of hemostats and fluoroscopy/imaging is used to assess the position of the cannula/stylet with regards to the vertebra. The hemostats are used to allow the hands of the user to be removed form the field in which the imaging radiation will be applied. With the aid of medical imaging (possibly applied along various trajectories), the cannula/stylet 24 are positioned with the desired orientation for passing into the body of the bone.

If the advancement of the stylet and cannula does not proceed along the intended pathway, the stylet 52 may be reversed rotated while preventing rotation of the cannula 42 to maintain it in position and remove the stylet. Then, a stylet as shown in FIG. 3C, may be employed. With beveled tip 58, the operator can rotate the sytlet to position the tip in a direction toward which he/she wishes to migrate the stylet. Once the orientation of the stylet 52 and cannula 42, having been advanced over the stylet, has been satisfactorily set, the fluoroscopy/imaging is discontinued, the hemoststs are removed and the operator carefully gasps the cannula/stylet being careful not to alter the orientation. The stylet with beveled tip 58 is then removed and replaced by the stylet with self-tapping threads 60. Grasping the combination handle 44/46, and optionally the cannula tube 48, the operator then proceeds to both push translationally and torque the combination handle to begin the threading the stylet end 60 into hard bone tissue.

After "biting" into the bone with a few turns of the self-tapping threads, the operator's hands are removed and the devices maintain their position by the support provided by the bone surrounding the threads. The devices/instruments are again viewed fluoroscopically of otherwise imaged both along the longitudinal axis of the cannula/stylet and laterally to determined the depth of the instruments. If the desired depth and placement has not yet been achieved, imaging is discontinued, and the cannula/stylet are further torqued or otherwise advanced into the cancellous bone until the tip of the cannula has been positioned in the desirable location.

Upon achieving the desired placement of the cannula at sat a site for treatment, the operator reverse rotates the stylet 52 to remove it from the cannula 42, while preventing rotation of the cannula. The cannula at this state is effectively press-fit into the bone site which aids the operator in preventing its rotation. Once the stylet has been completely removed for the cannula, fluoroscopic imaging/viewing of the cannula may optionally be performed to assure that the cannula did not move during the removal of the stylet.

Optionally, a contrast agent, e.g. a product known as OMNIPAQUE 300 available from Nycomed in Princeton, N.J., may be injected through the cannula and the flow of the contrast agent is viewed fluoroscopically or with other imaging in order to ascertain that the tip of the cannula has not been placed in a vein or other significant vessel. Preferably, the contrast agent is injected through tubing connected to the cannula. When tubing is used, it is preferably of a smaller length and diameter than tubing that is used for injection of implant material. Contrast agent must be flushed out of the site prior to injection of the implantation material, so it is preferable to inject only a small volume of the contrast agent. Viewing of the flow of the contrast agent helps to identify the shape of the body into which the injection of implant material is to be performed, as well as to locate where the major veins lie. After completing the flow of the contrast agent, the remnants of the contrast agent are flushed by injecting a flushing solution (e.g. saline) through the cannula tube 48, using a syringe or other injector. The imaging is preferably discontinued for this step. The contrast agent is flushed out so that it does not occlude, cloud, or otherwise compete with the viewing of the radiopacity of the implant material when it is placed.

Figures 4A, 4B:
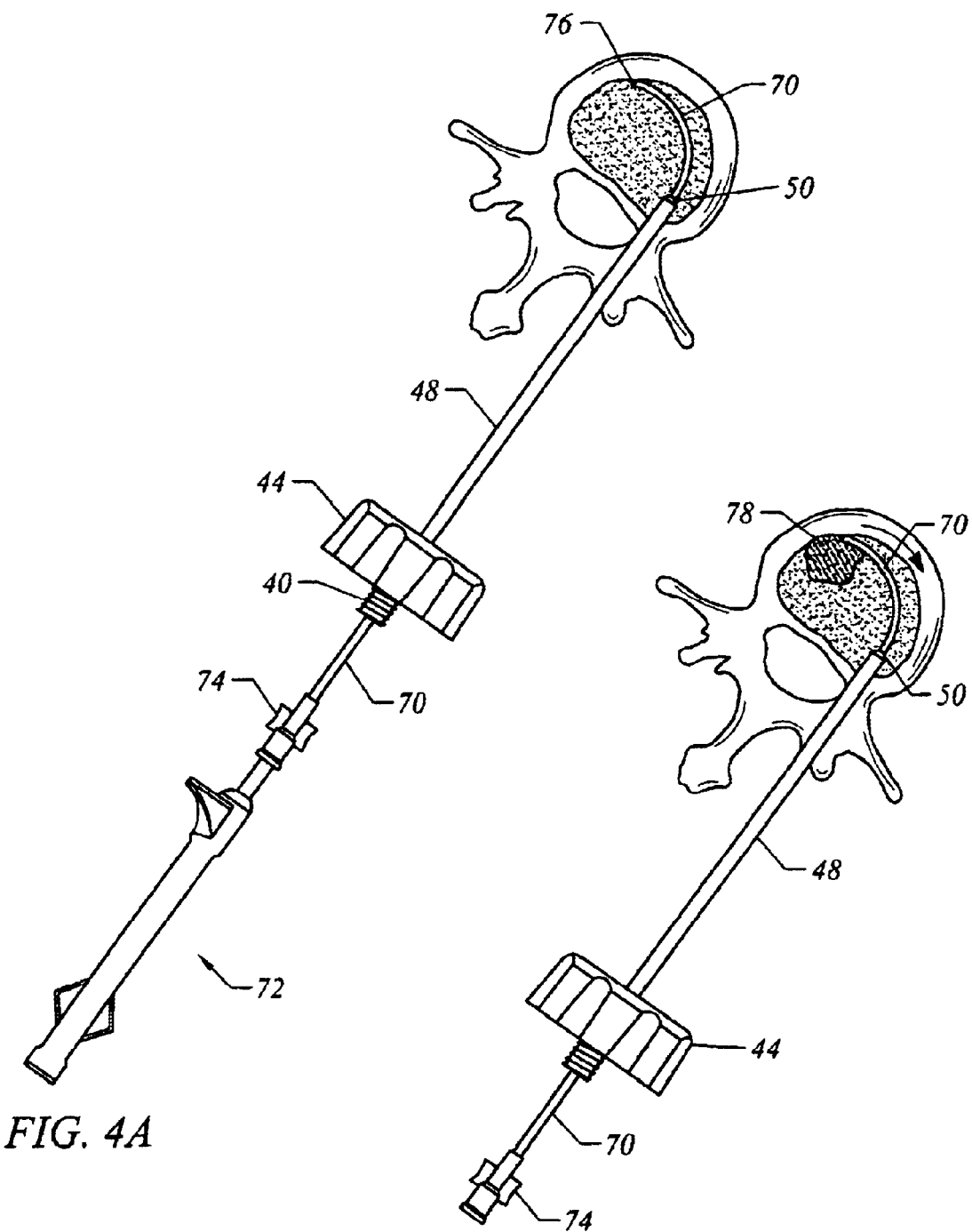
Figure 4C:
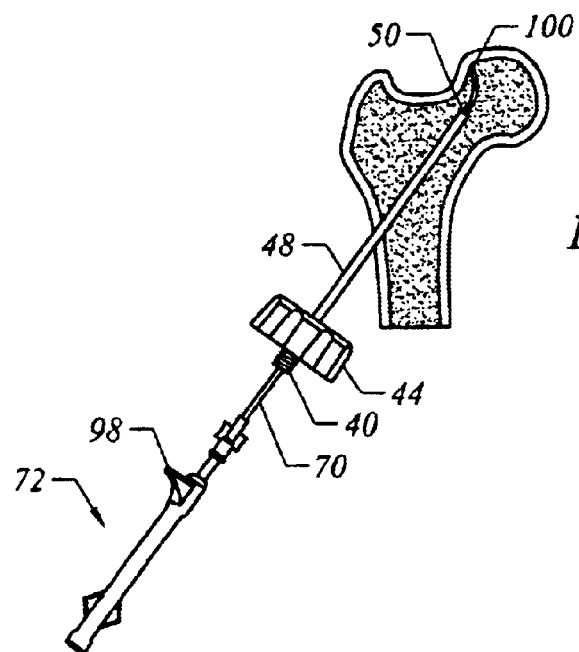
Figure 4E:
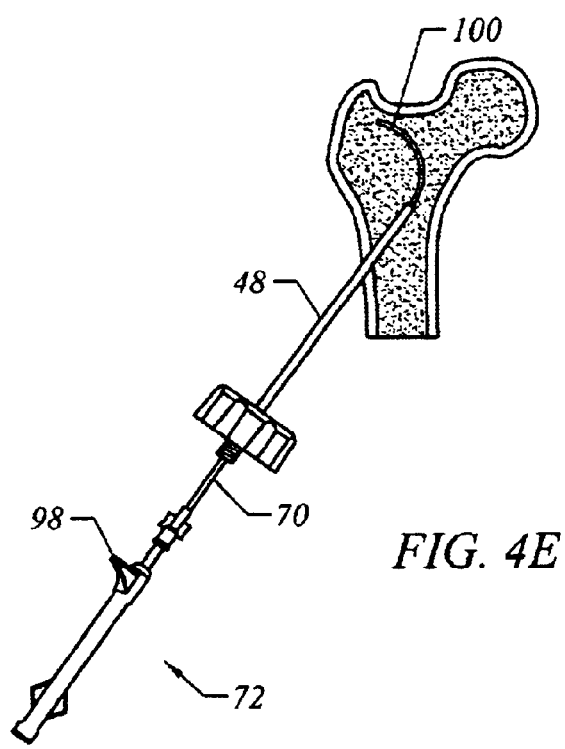
Figure 4D:
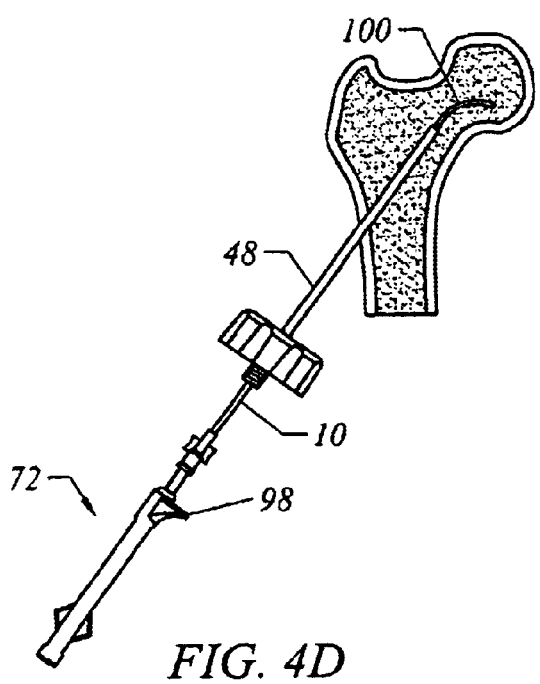

Whether or not such steps are taken to verify cannula placement at this stage, utilizing the present invention, it is possible to directly reach tissue sites as shown in FIGS. 4A–4C" with a tube 70 once the cannula 42 is set in place. (In either case, the verification steps taken above may be repeated or performed for the first time, but for the bone catheter described.)

The sites shown in FIGS. 4A–4C" are radially or remotely located from the distal end 50 of the cannula. They are reached by way of a catheter tube 70 which is received within and extend beyond cannula tube 48. In FIG. 4A, a manipulator 72 is shown received by the catheter 70, abutting catheter fitting 74. Details of the manipulator follow in connection with the description of FIGS. 5A–5C. Catheter fitting 42 may take the form of a luer fitting to interface either directly with conduit 22 or injector 20 at nozzle 36.

In either case, once emplaced, the extended conduit 70 allows an operator to reach sites removed from the access port formed by and aligned with the axis of the cannula. In FIGS. 4A and 4B, by tunneling through cancellous bone in the vertebral body, a site opposite the entry region of the catheter and the distal tip 50 of the cannula is available at the distal end 76 of catheter 70.

Generally, such a site will be reached by first advancing the manipulator member (or merely an internal core member or guide wire) and then advancing the catheter over the same or by simply advancing the manipulator and catheter together relative to cannula 42. For this purpose, the end of the manipulator (possibly the end of a core member or guide wire, but preferably the end of an obturator 140 integral with or placed over the manipulator) may include a tip or "beak" adapted for traversing cancellous bone tissue.

Once manipulator 72 (or any basic curved wire and/or any obturator placed therein) is removed, as shown in FIG. 4B, a bolus of implant material can be delivered.

This may be accomplished by connecting the applicator 20 directly or via conduit 22 to catheter fitting 74 and actuating the applicator. With the exemplary applicator shown, actuation is accomplished by rotating first and second columns, 26 and 28, relative to each other to cause drive piston 30 into vessel section 34 via threading 38 to expel flowable implant material.

By retracting catheter 70 in the direction of the arrow shown in FIG. 4B, most or all of the vertebral body can be filled with implant material. Retracting or drawing catheter 70 back in this manner while continuing to flow implant material therethrough offers a significant advantage over known approaches where both sides of a vertebral body (or another bony structure) need to be accessed to achieve the same coverage.

Another potential use of the catheter is illustrated in FIGS. 4C–4C". By rotating the manipulator used to control the trajectory of the catheter 70 as it is advanced beyond cannula tip 50 to pass or burrow through bone, different remote locations may be accessed. Each of FIGS. 4C, 4C' and 4C" indicate different access locations by virtue of the direction in which the catheter/manipulator is facing (as indicated by directional stop or handle 98) and the extent to which cannula body 48 is inserted in the bone. The trajectory of the catheter is preferably set or corrected by first withdrawing it and the internal manipulator into the cannula then adjusting the orientation, before re-penetrating the cancellous bone with the catheter and manipulator together or the manipulator alone. Such manipulation may be called for in light of the fact that access (or approach) within the cancellous may be limited by anatomy. That is to say, surrounding tissue (tendons, ligaments, arteries, sensitive organs, etc) or the morphology of the bone site itself may dictate taking any number of paths to reach a desired site.

For whatever reason, the present invention offers a solution to delivering implant material (or devices) to pin-point location(s) that may not feasibly be reached by a direct-line system. The curved or radially remote access options offered by the present invention are therefore particularly useful. Alternatively, or additionally, a retract-and-deliver approach may be utilized as described in connection with the action depicted in FIG. 4B in order to distribute delivery of material.

Regardless, a preferred assembled manipulator device 72 to assist in catheter end placement is shown in FIG. 7. The manipulator comprises a slotted housing 80 with an actuator or core wire 82 attached at a distal point 84 as depicted in FIG. 5B by dashed lines. A groove or slot 86 is configured to receive a slider member 88 such as that shown in FIG. 5C. The slider/slide handle may have one or more sections with a textured interface 90 to provide positive traction with the same. A hollow actuator sheath 92 is attached to slide handle 88 such that core/guide wire 82 may pass through the body of the sheath/handle combination.

To assemble the items as shown in FIG. 5A, sheath 92 is passed through a distal guide portion 94 of housing 80 and slide handle 88 is set within grove 86. Guide wire 82 is then set in place, affixed at point 84 as described above to secure the pieces.

Core/guide wire 82 preferably comprises Nitinol (NiTi alloy), another superelastic material or at least a highly flexible material such as noted above. In the variation of the actuator shown, core wire 82 includes a pre-set or pre-formed curved distal tip 96. Sheath 92 is configured to be more stiff or have greater stiffness than core wire 82. Still, as referenced variously herein, a core wire 82 may be used alone to guide catheter 70, or in connection with such hardware as shown in FIGS. 5A–5C.

When taken together, when slide handle 88 is retracted within slotted housing 80 as shown in FIG. 5A, sheath 92 is retracted to expose a curved end 96 of core member 82. This allows tip 96 to return to or take its pre-set or pre-formed shape. Upon advancing handle 88 as indicated in dashed lines in FIG. 5A, sheath 92 advances to force the core wire into a straightened configuration.

As alluded to with respect to FIGS. 4C–4C", by varying the direction in which the actuator 72 is oriented relative to cannula 42, the direction in which the catheter 70 (which overrides the actuator) is directed upon advancement from the end of the cannula may be varied. Stop or rest 98 may provide a visual indication in this regard as the catheter is forced or burrows through hard cancellous bone or other "hard" tissue, including cartilage.

Another feature may be employed as well in order to reach distinct sites (such as the locations indicated in FIGS. 4C–4C"). Namely, the extent of retraction/advancement of slide handle 88 within housing 80 may be controlled to vary the degree of curvature attained by the end 96 of core member 82 and hence an end 100 of catheter 70 which overrides the same.

FIG. 6 shows an exemplary catheter 70 as may be used in the present invention in isolation. It is shown with a pre-formed, curved end 100. With proper alignment, using such an end may provide assistance in reaching a curved state when traversing hard/bony tissue in connection with curved end 96 of core wire.

Whether provided with a curved end, or an initially straight end as shown in FIG. 8, when cannula 70 is set over manipulator 72 as shown in FIG. 7, the combination may be articulated from curved to straight depicted in like matter to that shown in FIG. 5A. Utilized in this manner, catheter positioning as shown in FIGS. 4A–4C may be achieved by setting the curvature of the catheter via the manipulator as desired and traversing or burrowing through tissue.

Note, however, that similar utility may be achieved absent the use of an actuator sheath. Catheter 70 may be set directly over the pre-formed core wire 82 used in isolation. In which case, cannula body 48 can be used as a restraining member, allowing the catheter and core wire to curve as indicated in FIGS. 4A–4C upon leaving the end 50 of the cannula. Note, however, that an actuator sheath/member may be required to achieve certain catheter placement or trajectories as desired.

Use of the actuator also offers certain control over the control wire that may be desired from the perspective of user safety and ease of handling. Still, where a core wire is used alone, for most applications it will store less energy and, hence, present less of a threat than the above-referenced Nitinol needle/tube employed by Cook Medical.

Where no actuator member is provided though, it is still generally preferred to attach the guide wire used to a handle or grip in one way or another. This can facilitate pointing or directional input as with grip/stop 98. Still, any wire used within catheter 70 may be directly manipulated (even by a loop or hook formed at the proximal end of the wire).

In addition, further variation is contemplated with respect to the end 100 of catheter 70. Any number of tip configurations 102 may be employed. For instance, the variation in FIG. 9A includes a radiopaque marker 104, such as a platinum band—the utility of which being well known to those with skill in the art. The variation in FIG. 9B includes a coring member 106 with a serrated edge 108. Bone tissue may be cut free by twisting catheter 70 within cannula 42, even relative to core wire 82. Such action may be useful for traversing bone or obtaining a biopsy sample. For such purposes, the serrated member preferably comprises stainless steel or titanium alloy. It may also serve a function as a marker band for fluoroscopic visualization of the catheter tip.

Another option is to employ a perfusion/drainage tip 110 including a plurality of perforations or orifices 112 within the catheter wall or a terminal element attached thereto. Still further, especially for the removal of soft tissue, a foreceps or nibbler 114 type device may be provided at the end of the catheter. Such a device may operate by way of sliding a member 116 with resilient jaws 118 that ride back and forth over a restraining tube 118, providing such action as indicated. Of course, other approaches as known in the art may be employed as well.

Another option for catheter 70 is to provide a modified fitting 74 at the proximal end of the device. Specifically, a dual input fitting 130 may be employed. In which case, a first orifice 132 could provide for receipt of the core wire 82 and/or actuator 72 while a second orifice 134 leading to a common lumen 136 may be used to introduce anything from flowable material to wire(s) or suture(s). Whether or not a multiple port fitting is provided, proximal fitting 74 may include wings 140 or similar structure to facilitate its angular manipulation.

Still further, an obturator may be used in connection with the present invention. A flexible member like obturator 140 shown in FIG. 11 may be employed to simply close-off catheter 70 upon removal of actuator 72 or core wire 82.

Yet another option is to provide an obturator 142 as shown in FIG. 12. This device comprises a rigid section 144 which may be tubular to receive a core wire and/or the distal end of actuator assembly 72. The proximal end 146 of the obturator/perforator preferably comprises driving features 148 such as gears or a knurled interface. The features may be driven by hand or by an auxiliary device (not shown). The distal end 150 of obturator/perforator 142 comprises a plurality of interlocking links 152. FIG. 13 shows a detail of the links. They are preferably regularly-shaped, repeating members (such as square or hexagonal segments) able to transmit torque applied to the drive futures to a working end 160 of the device.

The working end of the obturator may be configured in any number of manners. FIG. 14A is a close-up of a socket driver end 162 as seen in FIG. 13. FIG. 14B shows a screw driver attachment 164. FIG. 14C shows a cutter attachment in the form of a drilling, milling or grinding bit 166. FIG. 14D shows a wire twister device 168 including a wire capture groove 170. Other end configurations are possible as well.

In use, as alluded to above, the obturator may be over the actuator or a core wire. Alternately, it can be used within/guided by the catheter 70 alone upon removal of manipulator 72 or a mere core wire 82. Generally, it is integrated with the handle (for example by gluing it within the interior of guide portion 94) as indicated by the dashed line placement of FIGS. 5A and 5B.

The possible constructional options of the various devices or device elements discussed above should be apparent to one with skill in the art. Generally, biocompatible materials including plastics, and metal alloys including steel, stainless steel and titanium alloys are preferred. This being said, catheter body 70 preferably comprises PEEK, actuator sheath 92 preferably comprises stainless steel or titanium/titanium alloy as do the various obturator components shown and discussed. The various handle members, and pressure applicator/injector may comprise nylon or another suitable material. Preferred guide/core wire composition has already been discussed.

In terms of sizing, the relative sizing of members is highly variable. However sized, certain members will be configured for navigating though harder tissues—particularly cancellous, cortical bone and cartilage. Variations in sizing are contemplated such that the present invention may be used for introducing surgical or diagnostics devices, fluids exhibiting a wide range of viscosities, pastes and powders. Notwithstanding, in a device developed for effecting vertebroplasty or long bone augmentation (as in the examples shown) suitable attributes are about as follow:

| | |
|---|---|
| core wire 82 OD | 0.5 to 1.6 mm |
| conduit 70 ID | 1.2 to 3.7 mm. |
| conduit 70 OD | 1.5 to 4.7 mm. |
| actuator sheath 92 ID | 0.7 to 2.0 mm |
| actuator sheath 92 OD | 0.8 to 2.5 mm |
| obturator 140/142 ID | 0.9 to 2.8 mm |
| obturator 140/142 OD | 1.2 to 3.7 mm |
| cannula 48 ID | 1.5 to 4.7 mm. |
| cannula 48 OD | 2.0 to 6.1 mm. |

Wall thickness of the various members may, of course, be derived from the dimensions presented. The length of conduit 70 and actuator 72/guide wire 82 may be set so as to reach sites distal of cannula end 50 by between about 0 and about 100 mm. An ability to reach sites between about 0 and 50 mm lateral of a cannula tip emplaced in cortical bone may be especially useful in vertebroplasty procedures Naturally, the particular configuration of the respective elements will vary according to the task that the hardware is applied. Of course, accessing a more remote location may be possible with the present invention as may any of the other applications noted and still others.

Though the invention has been described in reference to several examples, optionally incorporating various features, the invention is not to be limited to what is described or indicated as contemplated with respect to each variation. The breadth of the present invention is to be limited only by the literal or equitable scope of the following claims. That being said,

We claim:

1. A bone access system comprising:
   a cannula, said cannula adapted for driving through compact bone tissue,
   a flexible conduit, said conduit adapted to be slidably received within said cannula, and
   a core wire, said core wire adapted to be slidably received within said flexible conduit and including a distal portion having a pre-formed curve,
   wherein, together, said core wire and said flexible conduit are adapted to be advanced from a distal end of said cannula to form a curved path and an actuator sheath provided between said core wire and said flexible conduit, said actuator sheath configured to selectively straighten said pre-formed curve upon advancement over the same.

2. The system of claim 1, wherein said conduit is adapted to deliver hard tissue implant material to a site upon removal of said core wire therefrom.

3. The system of claim 1, further comprising a stylet having a head adapted for passing through compact bone tissue.

4. The system of claim 1, further comprising a slotted housing and a handle slidably received within said housing, wherein said handle is attached to said actuator sheath and said core wire is attached to said housing proximal to said handle.

5. The system of claim 1, further comprising an obturator positioned over said actuator sheath and inside said conduit.

6. The system of claim 5, wherein said obturator is affixed to said handle.

7. The system of claim 5, wherein said obturator comprises rigid section and a flexible distal end portion.

8. The system of claim 7, wherein said obturator end portion comprises a plurality of links, wherein said links are adapted to be drivable.

9. The system of claim 8, wherein said obturator end portion further comprising an active distal tip including a member selected from a group consisting of drivers, cutters and twisters.

10. The system of claim 9, wherein a proximal end of said obturator includes a drive interface.

11. The system of claim 1, wherein said conduit further comprises an active distal tip selected from a group consisting of serrated, radio-marked, perforated infusion and snipper tips.

12. The system of claim 1, sized to effect vertebroplasty.

13. The system of claim 1, further comprising a high pressure applicator for delivering hard tissue implant material through said conduit.

14. The system of claim 1, wherein radial extension of said conduit from said cannula up to about 50 mm is possible.

15. The system of claim 1, wherein longitudinal extension of said conduit from said canula up to about 100 mm is possible.

16. A method of bone access comprising:
    advancing a cannula through bone tissue in a substantially straight path; and
    advancing a steerable member inserted in said cannula through bone tissue in a path that extends radially from an axis of said cannula,
    wherein said steerable member comprises a flexible conduit and a core wire having a preformed curve, said core wire adapted to direct said conduit in said radially-extending path upon release from a substantially straight, constrained state.

17. The method of claim 16, accomplished with a system as described in any one of claims 2, 3 and 4∝13.

* * * * *